United States Patent
Hogg

[11] 3,982,182
[45] Sept. 21, 1976

[54] CONDUCTIVITY CELL FOR PARTICLE STUDY DEVICE

[75] Inventor: Walter R. Hogg, Miami Lakes, Fla.

[73] Assignee: Coulter Electronics, Inc., Hialeah, Fla.

[22] Filed: Jan. 21, 1975

[21] Appl. No.: 543,011

Related U.S. Application Data

[63] Continuation-in-part of Ser. No. 387,548, Aug. 13, 1973.

[52] U.S. Cl. ............................................. 324/71 CP
[51] Int. Cl.² ........................................... G01N 27/00
[58] Field of Search ..................... 324/71 CP; 73/32

[56] References Cited
UNITED STATES PATENTS
3,706,030  12/1972  Klein et al. ..................... 324/71 CP FOREIGN PATENTS OR APPLICATIONS
274,474  6/1970  U.S.S.R. ................................. 73/32

OTHER PUBLICATIONS
"Compensation of the Temperature and Concentration Errors of Conductivity Granulometers", Bebyakou Physiochemical Measurements, pp. 1218–1222, translated from Izmeritelnaya Tekhnika No. 8, pp. 58–60, Aug. 1972, Plenum Publishing Corp., New York.

Primary Examiner—R. V. Rolinec
Assistant Examiner—Vincent Sunderdick
Attorney, Agent, or Firm—Silverman & Cass, Ltd.

[57] ABSTRACT

The conductivity cell is utilized in a particle study device of the type wherein liquid electrolyte containing particles is caused to traverse an electrical sensing zone of small dimensions, sensing electrodes being located on either side of the sensing zone. The conductivity cell includes two electrodes situated in the electrolyte and being coupled to an electrical sensing circuit including the sensing electrodes. The resistance across the sensing electrodes and the resistance across the conductivity cell electrodes are connected in series with the power source and function as a voltage divider. The junction between the two resistances is coupled to a signal detecting amplifier so that a change in the conductivity of electrolyte will cause a change in both of the resistances whereby the voltage at the junction between the two resistances is essentially constant. To obtain a relatively high resistance between the conductivity cell electrodes, the conductivity cell includes a long and narrow column of electrolyte between the conductivity cell electrodes. In one embodiment, the long and narrow column of electrolyte is situated in a length of serpentine tubing.

15 Claims, 3 Drawing Figures

CONDUCTIVITY CELL FOR PARTICLE STUDY DEVICE

CROSS-REFERENCE TO RELATED APPLICATION

This application is a continuation-in-part of my earlier copending application, Ser. No. 387,548, filed on Aug. 13, 1973. Both applications are assigned to the same assignee.

BACKGROUND AND SUMMARY OF THE INVENTION

The present invention relates to improvements in a conductivity cell utilized in a particle study device. An example of such a conductivity cell is disclosed in Russian Pat. No. 274,474.

In the field of particle study devices it is common for a liquid electrolyte containing particles to be moved through a sensing zone. Each particle traversing the sensing zone generates an electrical signal. However, changes in the conductivity of the electrolyte alter the signals. In the well known COULTER particle study device the sensing zone includes an aperture located in the wall of a vessel situated within another vessel, sensing electrodes are situated on either side of the aperture and mechanisms are provided for causing, and for monitoring the amount of, fluid flow through the aperture. As a particle flows through the aperture it causes a change in the electric field and the electric current between the sensing electrodes. This change is picked up by a signal-detecting circuit and the signal produced thereby is amplified and referred to as a particle pulse. (The mark COULTER is a registered trademark, No. 995,825 of Coulter Electronics, Inc. of Hialeah, Florida.)

Heretofore it has been proposed to insert another electrode into one of the bodies of liquid electrolyte so as to form a resistance between that electrode and with either one of the sensing electrodes or with a fourth electrode inserted in one of the bodies of electrolyte. The resistance between the third electrode and either one of the sensing electrodes or the fourth electrode is then connected into the electrical sensing circuitry for the particle analyzing device in such a manner as to compensate for changes in electrolyte conductivity.

According to the invention there is provided, in a particle study device wherein a liquid electrolyte containing parties is caused to traverse an electrical sensing zone of small dimensions and wherein the device has a conductivity cell including two electrodes in the electrolyte for establishing a variable resistance which is a function of the conductivity of the electrolyte and which is connected to the electrical sensing circuit including the sensing zone to provide compensation for changes in electrolyte conductivity, a conductivity cell which includes a long, narrow column of electrolyte between the conductivity cell electrodes with each of the conductivity cell electrodes being in contact with the electrolyte at one end of the column.

The conductivity cell preferably includes a long tube or tubing which may be straight or coiled and the long and narrow column of electrolyte is situated within the tubing. A conductivity cell including such a long narrow column of electrolyte provides a much larger resistance in the conductivity cell thereby to compensate better for changes in the conductivity of the electrolyte.

DESCRIPTION OF THE PREFERRED EMBODIMENTS

The present invention teaches the provision of a long and narrow column of electrolyte in a conductivity cell utilized in a particle study device. A particle study device utilizing a long column of electrolyte between two electrodes of a conductivity cell is disclosed in the earlier application, Ser. No. 387,548, referred to above. More specifically, FIG. 17A in the earlier application illustrates a conductivity cell including a section of serpentine tubing having electrolyte therein forming a long narrow column of electrolyte. Electrodes are situated within the tubing at either end thereof and one electrode is situated within the tubing in the middle thereof. As described in the earlier application, this conductivity cell is particularly adapted for use in the particle study device shown in FIG. 17 of the earlier application and as a form of conductivity cell which is isolated from the electrolyte in the vessels of the particle study device. Accordingly so far as the disclosure in the earlier application relates to the present invention such disclosure is incorporated herein by reference.

Figure 1:
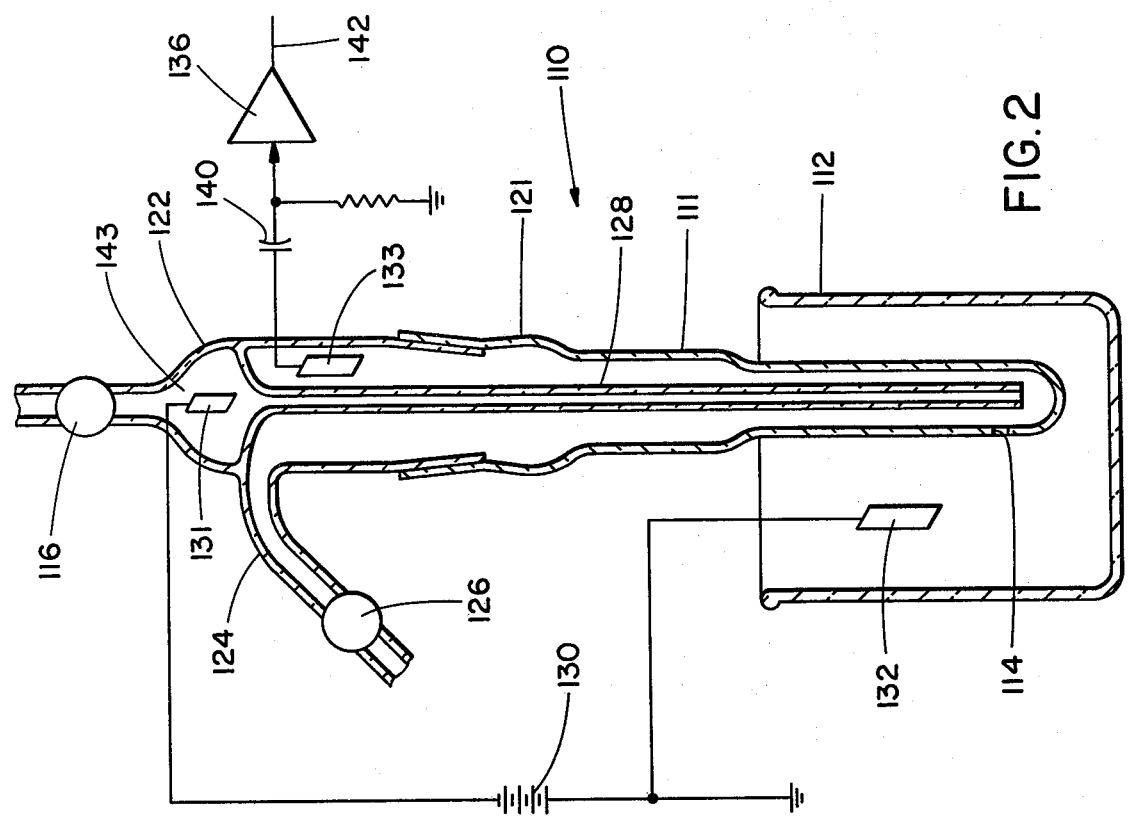
FIG. 1 is a diagram partially schematic and partially in section of a portion of a particle study device including a conductivity cell constructed in accordance with the teachings of the present invention.

Referring now to FIG. 1, reference numeral 10 generally designates the sensing structure of a particle study device and a portion of the associated electrical sensing circuit therefor. This structure includes an elongate first vessel or tube 11 which is situated within a larger second vessel 12, each of the vessels 11, 12 having a liquid electrolyte therein. The liquid electrolyte in the second vessel 12 also contains particles to be studied. The first vessel 11 is arranged in a generally vertical position. Near the lower end of the first vessel 11 there is an aperture 14 in the wall of the vessel 11 which, because of the aperture therein, is commonly referred to as an aperture tube. The aperture 14 is microscopic in size and is only slightly larger than the particles which flow through the aperture when liquid electrolyte is caused to flow from the second vessel into the first aperture tube 11. For the purpose of illustration, in the drawings the aperture 14 is shown enlarged. To cause liquid to flow from the second vessel 12 into the tube 11 the upper end of the aperture tube 11 is connected to a source of vacuum through a valve 16.

In the illustrated embodiments, the aperture tube 11 is composed of two separable sections 21 and 22. The lower section 21 has the aperture 14 therein and the upper section 22 is connected to the valve 16. Also in accordance with the teachings of the present invention the upper section 22 has a conduit 24 extending therefrom for connection through a valve 26 to a source of liquid electrolyte. In the particular embodiment illustrated in FIG. 1, this conduit 24 has an enlarged portion or chamber 27 which extends through the upper section 22 into the interior of the tube 11. This conduit 24 then narrows to an elongate tube 28 which extends downwardly generally coaxial with the vertical axis of the tube 11.

As shown in FIG. 1, the electrical sensing circuit includes a power supply 30, a first electrode 31 situated within the chamber 27, a second electrode 32 situated in the second vessel 12, a third electrode 33 situated in an upper chamber 34 within the upper section 22 and a voltage sensitive detecting amplifier 36. The first electrode is connected to one side of power supply 30 and the second electrode is connected to a common conductor which in turn is connected to the other side of the power supply 30. The third electrode is coupled through a capacitor 40 to the amplifier 36.

From a study of the circuit connections shown in FIG. 1, it will be apparent that a conductivity cell is formed by the electrodes 31 and 33 and the electrolyte therebetween including a long narrow column of electrolyte within the tube 28. A resistance, which is essentially the resistance through the aperture 14 is established in the electrolyte between the electrodes 32 and 33. Accordingly, between the electrodes 31 and 32 and including the electrode 33 there are two resistances, the first resistance being the resistance of the conductivity cell between electrodes 31 and 33 and the second resistance being the sensing or aperture resistance between the electrodes 33 and 32. This second or aperture resistance varies as particles flow through the aperture. The electrodes 32 and 33 constitute sensing electrodes and electrodes 31 and 33 constitute conductivity cell electrodes.

The electrode 33 serves a dual purpose as both a conductivity cell electrode and a sensing electrode. Also, it will be apparent that the resistances between electrodes 31, 33 and 33, 32 function as a voltage divider and the voltage at the junction therebetween, i.e., at electrode 33, is coupled through the capacitor 40 to the sensing amplifier 36. Each time a particle passes through the aperture 14 the resistance between the electrodes 32 and 33 will vary and this change in resistance will cause the generation of a change in voltage which is passed through the AC coupling capacitor 40 to the amplifier 36 where the change is amplified to produce a particle pulse at the output 42 of the amplifier 36.

With the arrangement of electrodes and the circuit connections thereof described above, as electrolyte conductivity changes the resistances between electrodes 31, 33 and 33, 32 will vary. However, in the circuit disclosed, the voltage impressed on the amplifier 36 will remain essentially constant for slow changes of electrolyte conductivity.

Let $R_s$ stand for the (series) resistance of the conductivity cell, i.e., the resistance between electrodes 31 and 33, $R_{ap}$ represent the aperture resistance, and E represent the voltage of the power source. Then the aperture current $I_{ap}$ is $$I_{ap} = \frac{E}{R_s + R_{ap}}. \qquad (1)$$

It has been shown that the change of resistance $\Delta R$ due to the passage of a particle is $$\Delta R = \rho \frac{v}{A_{ap}^2} \qquad (2)$$

wherein $\rho$ is electrolyte resistivity, $A_{ap}$ is the cross-sectional area of the aperture and $v$ = particle volume. But $$R_{ap} = \rho \frac{l_{ap}}{A_{ap}} \qquad (3)$$

and $$R_s = \rho \frac{l_{cc}}{A_{cc}} \qquad (4)$$

neglecting end effects and where $l_{cc}$ and $A_{cc}$ are the length and equivalent cross-sectional area of the conductivity cell, and where $l_{ap}$ is the length of the aperture.

The signal voltage impressed on the amplifier 36 due to a particle passage is $$e_s = \Delta R I_{ap} \left[ \frac{R_s}{R_{ap} + R_s} \right]. \qquad (5)$$

Substituting values of $\Delta R$, $I_{ap}$, $R_s$ and $R_{ap}$, we have $$e_s = \rho \frac{v}{A_{ap}^2} \cdot \frac{E \cdot \rho \frac{l_{cc}}{A_{cc}}}{\rho^2 \left(\frac{l_{ap}}{A_{ap}} + \frac{l_{cc}}{A_{cc}}\right)^2} = \frac{E v}{A_{ap}^2 \left(\frac{l_{ap}}{A_{ap}} + \frac{l_{cc}}{A_{cc}}\right)^2}$$

which reduces to $$e_s = \frac{E \, l_{cc} \, A_{cc} \, v}{(l_{ap} A_{cc} + l_{cc} A_{ap})^2} \qquad (6),$$

independent of $\rho$. As a result, the signals generated by particles flowing through the aperture 14 and picked up by the amplifier 36 will be substantially independent of electrolyte conductivity.

Also in accordance with the teachings of the invention a substantial resistance is provided between the electrodes 31 and 33 through the tube 28, i.e., the conductivity cell includes a high resistance by reason of the long and narrow column of electrolyte confined within the tube 28.

Figure 2:
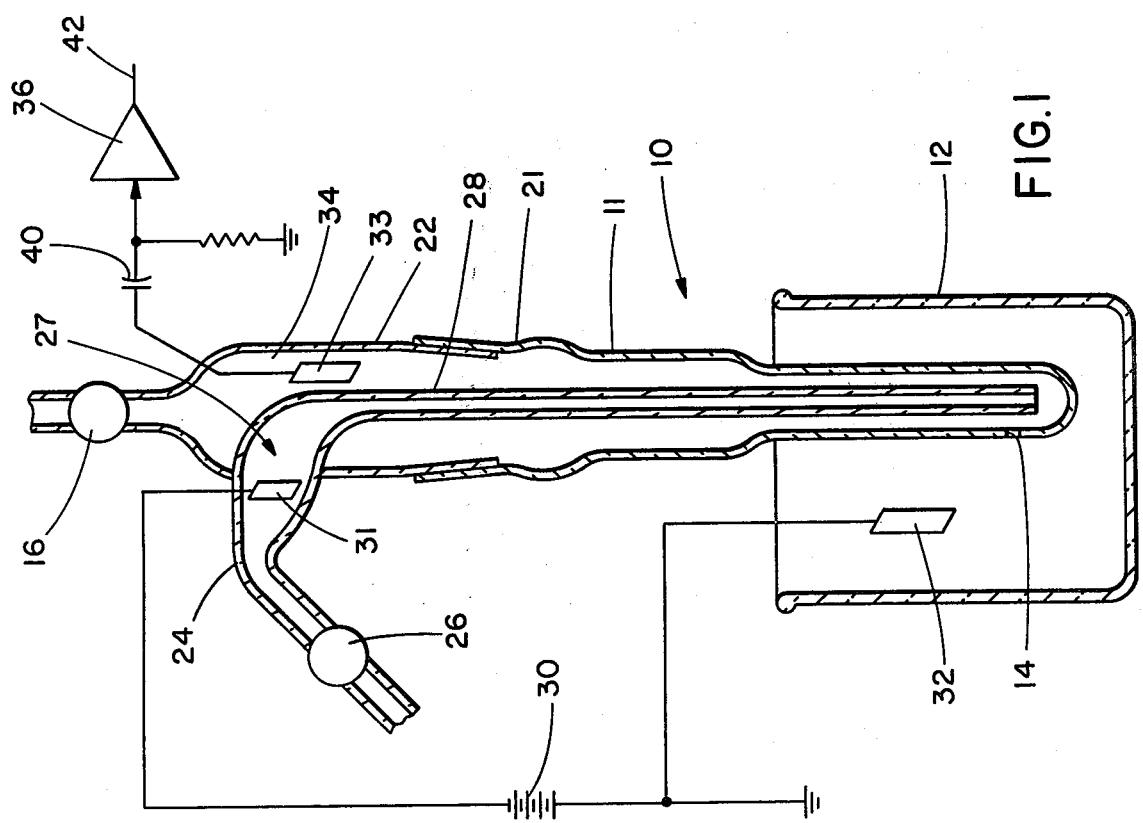
FIG. 2 is a diagram similar to FIG. 1 showing a modified construction of the device shown in FIG. 1.

In FIG. 2 there is illustrated an electrical sensing apparatus 110 which is substantially identical to the apparatus 10 shown in FIG. 1. In this respect, the apparatus 110 includes: a first vessel or aperture tube 111, a second vessel 112, an aperture 114, a valve 116, a lower section 121 and an upper section 122 forming the tube 111, a tubing or conduit 124 connected to a source of electrolyte through a valve 126, a tube 128 generally coaxial with the tube 111, a power supply 130, a first electrode 131, a second electrode 132, a third electrode 133, a detecting amplifier 136, a coupling capacitor 140, and an amplifier output 142. These elements correspond substantially to the similarly named elements in FIG. 1. The major difference between the apparatus 110 shown in FIG. 2 and the apparatus 10 shown in FIG. 1 is that the upper end of the tube 128 is not connected to the conduit 124 leading to the source of electrolyte, as in FIG. 1. Instead, the upper end of the tube 128 is connected to the upper end of the upper section 122. As shown, the upper end of the tube 128 flares outwardly and is secured to the inner walls of the upper section 122 thereby to form a chamber 143 at the upper end of the upper section 122 of the tube 111. It will be noted that the electrode 131 is situated in this chamber 143 in a manner similar to the position of electrode 31 in the chamber 27 at the upper end of the tube 28 in FIG. 1. The tube 128, of course, serves the same function as the tube 28 shown in FIG. 1, namely, to confine a long narrow column of electrolyte which provides a relatively high resistance for the conductivity cell which includes the electrolyte in the tube 128 and the electrodes 131 and 133. In all other respects the apparatus 110 is constructed and operates in substantially the same manner as the apparatus 10 shown in FIG. 1.

It will be understood that the tubes 28 and 128 not only serve to confine a quantity of electrolyte in a long narrow column thereby to provide a high resistance for a conductivity cell, but also are so situated as to be useful for educing or withdrawing liquid from the aperture tube 11 or 111 either by siphoning through the valve 26 or by vacuum through valve 116.

Figure 3:
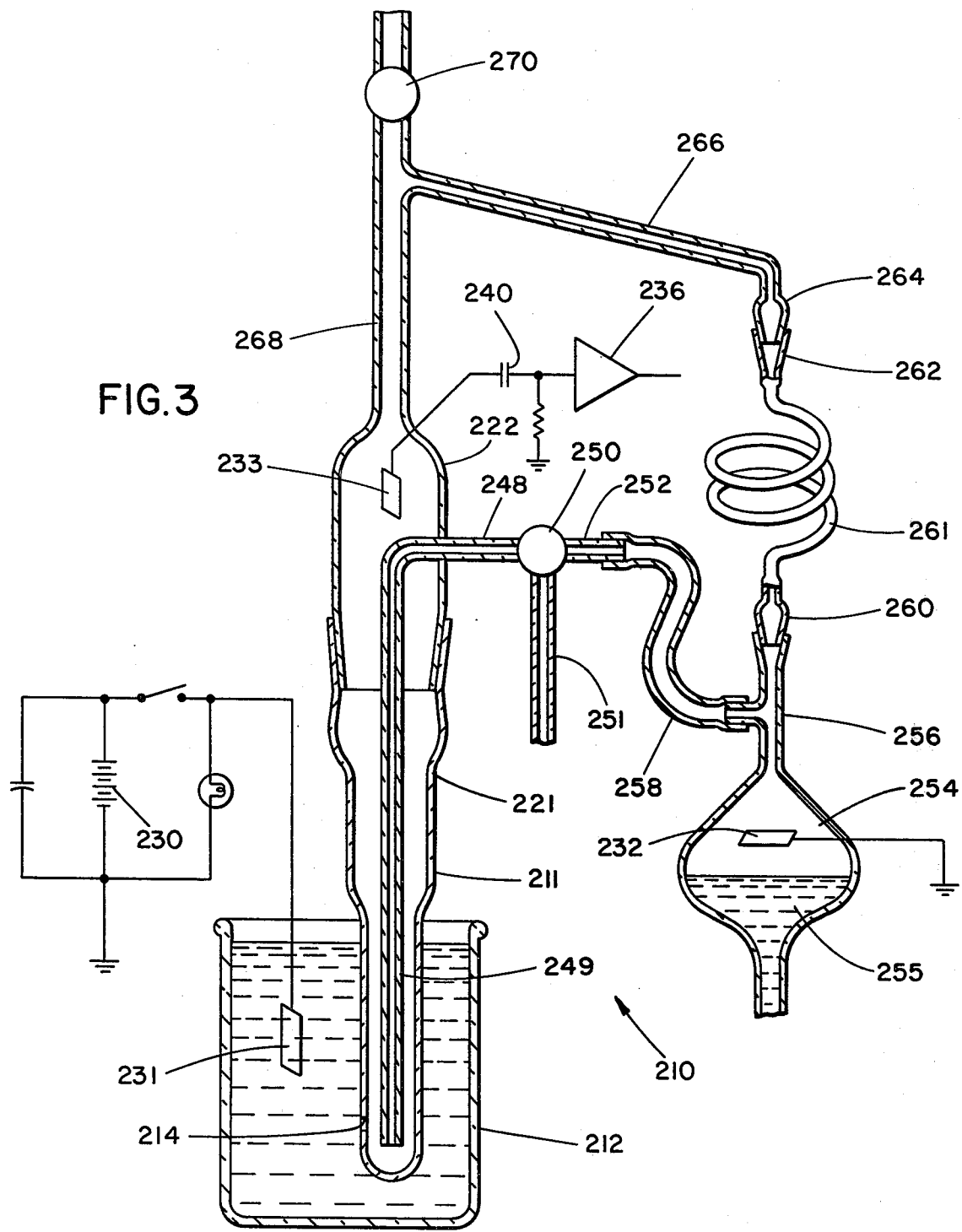
FIG. 3 is a diagram partially schematic and partially in section of electrical sensing circuit and glassware for a particle study device utilizing a conductivity cell constructed in accordance with the teachings of the present invention and including a section of serpentine tubing.

Referring to FIG. 3, another form of sensing apparatus is generally identified by the reference numeral 210. This apparatus 210 is similar in many respects to the apparatus 10 shown in FIG. 1 and includes a first vessel or tube 211, a second vessel 212, an aperture 214 in the wall of the first vessel 211, which is also formed of a lower section 221 and an upper section 222, a power supply 230 and three electrodes 231, 232 and 233 which function as sensing and conductivity cell electrodes in the same manner as electrodes 31, 32 and 33. In this embodiment, a major portion of the conductivity cell is exterior to the aperture tube 211. As shown, a conduit 248 is fixed to and extends through the upper section 222 and has a depending portion 249 which extends downwardly into the lower section 221. The conduit 248 is connected to a three-way valve 250 which is connected to a conduit 251 leading to a source of electrolyte and a conduit 252 connected to the upper chamber 254 of a manometer system which can be of the type disclosed in U.S. Pat. No. 2,869,078. A quantity of mercury generally identified by the reference number 255 is received in the chamber 254. A T-shaped glass tubing 256 has a lower leg thereof connected to the upper end of the chamber 254. A lateral leg is connected to a detachable flexible tubing 258 which is also connected to the conduit 252. The upper leg of the tubing 256 is flared for receiving a glass fitting 260. A serpentine tubing or glassware extends from the glass fitting 260 to an upper glass fitting 262 which has received therein another glass fitting 264 at the end of a tube or conduit 266. The conduit 266 communicates with a tubing 268 which extends upwardly from and is connected to the upper section 222. Above the connection of the conduit 266 to the conduit 268, the conduit 268 is connected to a valve 270 which is also connected to a source of vacuum not shown. As shown the electrode 232 is situated in electrolyte above the mercury 255 in the chamber or reservoir 254.

It will be apparent from the foregoing description of FIG. 3, that the conductivity cell is between the electrodes 233 and 232, and the aperture resistance is between electrodes 231 and 233. This is the opposite of the circuit connections shown in FIGS. 1 and 2. In other words, the position of the two resistances of the voltage divider circuit formed within the electrolyte are reversed. As shown, the electrode 233 connected to the junction is coupled through a capacitor 240 to a detecting amplifier 236.

The location of the liquid series resistance between electrodes 233 and 232 through the long, narrow column of electrolyte in the serpentine tubing 261 and between the upper section 222 and the chamber 254 of the manometer metering system, simplifies the construction of the upper section 222 commonly referred to as a control piece. It also enables one to use a different size of aperture tube and facilitates the changing of the liquid resistance, i.e., the length of the tubing 261 to maintain the best relationship to the resistance through the aperture 214 in the tube 211. Also, the aperture tube 211 can be easily replaced by performing the following sequence of steps:

1. Disconnect the vacuum from the valve 270 and open the valve 270. Next, the connection of the conduit 251 to the source of electrolyte is broken and the valve 250 is operated to connect conduit 251 to conduit 248 so that electrolyte in the tube 211 can be siphoned out through the conduit 251.

2. Replace lower section 221 of aperture tube 211.

3. The conduit 251 is now reconnected to the source of electrolyte and valve 270 is operated to apply vacuum to conduit 268. Then the valve 250 is operated to connect conduit 251 to conduit 252 so that the liquid resistor of the conductivity cell can be filled with electrolyte, i.e., so that the tubing 261 can be filled with electrolyte.

4. Position valve 250 to connect tubes 248 and 251. Electrolyte is sucked up through valve 270 via tube 249, quickly filling aperture tube 211 with electrolyte. The length of tube 249 facilitates washing out particles which have already been measured and which have accumulated at the bottom of tube 211.

5. Next, the valve 250 is put in a neutral position so that none of the conduits 248, 251 and 252 is in communication with any of the other conduits. The valve 270 is still open and connected to the source of vacuum for the purpose of setting threshold levels. In this respect electrode 232 serves a dual purpose as one of the electrodes of the manometer metering system in addition to serving as one of the conductivity cell electrodes. Then the valve 270 is closed thereby disconnecting the vacuum from the conduit 268 and the mercury 255 is allowed to descend in the manometer metering system thereby to start a study of particles in the liquid electrolyte in the vessel 212.

From the foregoing description, it will be apparent that the structure of the present invention provides a number of advantages and primarily the provision of a conductivity cell which has a high resistance defined by a long and narrow column of electrolyte confined within a long narrow tubing.

What is desired to be secured by U.S. Letters Patent is:

1. In a particle study device wherein a liquid electrolyte containing particles is caused to traverse an electrical sensing zone of small dimensions and wherein said device has a conductivity cell including two electrodes in the electrolyte for establishing a variable resistance which is a function of the conductivity of the electrolyte and which is connected to an electrical sensing circuit including the sensing zone to provide compensation for changes in electrolyte conductivity, the improvement comprising said conductivity cell including a long and narrow column of electrolyte between said electrodes with each of said electrodes being in the electrolyte at opposite ends of said column.

2. The particle study device according to claim 1 wherein said long and narrow column is defined by a length of serpentine tubing.

3. The particle study device according to claim 1 wherein said sensing zone is defined by an aperture in the wall of an elongate first vessel situated in a larger second vessel, each vessel containing liquid electrolyte, a long narrow tube being situated in said elongate first vessel and being filled with a column of electrolyte which defines said long and narrow column of electrolyte forming part of said conductivity cell.

4. The particle study device according to claim 3 wherein the electrical sensing circuit includes first and second electrodes, said first electrode being situated in said first vessel and said second electrode being situated in said second vessel, said first electrode also constituting one of said conductivity cell electrodes, and wherein the electrolyte at one end of and communicating with the interior of said elongate tube is isolated from the remaining electrolyte in said first vessel and the other of said conductivity cell electrodes is situated in the isolated electrolyte communicating with the interior of said tube.

5. The particle study device according to claim 4 wherein said isolated electrolyte communicating with the interior of said tube is in a chamber within said first vessel and said chamber is connected through a valve to a source of electrolyte.

6. The particle study device according to claim 4 wherein said isolated electrolyte in said first vessel is located in a chamber within said first vessel and said chamber is connected through a valve to a source of vacuum.

7. The particle study device according to claim 3 wherein the electrical sensing circuit includes a power supply, a first electrode in said second vessel connected to one side of said power supply and constituting a sensing electrode, a second electrode forming one of the conductivity cell electrodes, being in contact with the electrolyte at one end of said elongate tube and being connected to the other side of said power source, and a third electrode which is in the electrolyte in said first vessel at the other end of said tube, which constitutes the other conductivity electrode and which is coupled to a voltage sensitive amplifier, the resistance between the second and third electrodes constituting the conductivity cell resistance and the resistance between the first and third electrodes constituting essentially the resistance across the sensing aperture, and said two resistances forming essentially a voltage divider with the amplifier being coupled to a junction in the divider such that, when the conductivity of the electrolyte changes, the D.C. voltage at the junction in the divider formed by the two resistances will be essentially constant.

8. The particle study device according to claim 1 including an elongate first vessel having an aperture in the wall thereof and being situated in a second vessel, the aperture forming part of said sensing zone and each of the vessels having liquid electrolyte therein, a first chamber at one end of said first vessel, said chamber being connected to a valve which is also connected to a source of vacuum and to one side of said conductivity cell, the other side of said conductivity cell being connected to a manometer system and to a valve connected to a source of electrolyte and connected to a conduit extending into said first vessel.

9. The particle study device according to claim 8 wherein said conductivity cell includes a serpentine tubing of small diameter the electrolyte in said tubing constituting said long and narrow column of electrolyte between the electrodes of said conductivity cell.

10. The particle study device according to claim 8 wherein said electrical sensing circuit for said particle study device includes a power supply, a first electrode connected to one side of said power supply and situated within the electrolyte in said second vessel, a second electrode situated in a second chamber at another end of said conductivity cell and connected to a common conductor connected to the other side of said power supply, a third electrode in said first chamber of said first vessel and coupled to a signal detecting amplifier, the resistance between said first and third electrodes consisting essentially of the resistance through the aperture which varies when a particle passes through the aperture and the resistance between said second and third electrodes being the resistance of said conductivity cell, the amplifier being coupled to the junction between the two resistances which together function as a voltage divider, each of these resistances being a function of the conductivity of the electrolyte and changing when the conductivity of the electrolyte changes and in such a manner that the D.C. voltage at the junction therebetween remains essentially constant so that the signals picked up by the signal detecting amplifier are substantially independent of the conductivity of the electrolyte.

11. The particle study device according to claim 9 wherein the ends of said serpentine tubing are detachably connected to said first chamber and to said manometer system thereby to permit said serpentine tubing easily to be replaced for adjusting the resistance of the conductivity cell relative to the resistance across the aperture.

12. The particle study device according to claim 3 wherein said tube is coaxial with said first vessel thereby to permit said tube easily to be utilized as a conduit for educing liquid from said first vessel.

13. A particle study device including a conductivity cell, said device and cell having a plurality of electrodes; a first pair of said electrodes being positioned at opposite ends of an electrical sensing zone of small dimensions through which particles in a liquid electrolyte are caused to traverse, there being a first resistance between said first pair of electrodes; said conductivity cell having a second pair of electrodes immersed in electrolyte, said second pair of electrodes establishing a second resistance which is a variable function of the conductivity of the electrolyte and which is connected to an electrical sensing circuit including said sensing zone to provide compensation for changes in electrolyte conductivity; said second resistance being much larger than first resistance and said two resistances forming a voltage divider having a junction such that, when the conductivity of the electrolyte changes, the D.C. voltage at said junction will be essentially constant.

14. The particle study device according to claim 13 in which said two pairs of electrodes comprise three electrodes, one of which belongs to both of said pairs and is at said junction.

15. The particle study device according to claim 13 in which said electrodes of said second pair of electrodes are spaced apart by a long column of the electrolyte for defining said second resistance.

* * * * *